United States Patent
Shiau et al.

[11] Patent Number: 6,051,246
[45] Date of Patent: Apr. 18, 2000

[54] ANTIMICROBIAL COMPOSITION SUPPORTED ON A HONEYCOMB-SHAPED SUBSTRATE

[75] Inventors: Yen-Kuen Shiau, Taipei; Chung-Hsun Wu, Tao-Yuan, both of Taiwan

[73] Assignee: Parker Holding Services Corp., Taipei, Taiwan

[21] Appl. No.: 09/046,834

[22] Filed: Mar. 25, 1998

[30] Foreign Application Priority Data

Mar. 28, 1997 [TW] Taiwan .................................. 86103892

[51] Int. Cl.⁷ .................................................. A01N 25/26
[52] U.S. Cl. .......................... 424/409; 424/417; 424/419; 424/420; 424/421; 424/682; 424/691; 424/692
[58] Field of Search .......................... 510/445; 424/405, 424/682, 691, 692, 408, 409, 417–421

[56] References Cited

U.S. PATENT DOCUMENTS

| | | | |
|---|---|---|---|
| 57,174 | 8/1866 | Napier | 424/682 |
| 3,234,075 | 2/1966 | Braitberg | 424/692 |
| 3,399,136 | 8/1968 | Bell | 424/692 |
| 3,476,692 | 11/1969 | Hoffmann | 424/691 |
| 3,510,222 | 5/1970 | Schmank et al. | 424/692 |
| 4,293,540 | 10/1981 | Saukita | 424/691 |
| 4,377,675 | 3/1983 | Daudt et al. | 508/25 |
| 5,110,784 | 5/1992 | Williams et al. | 502/401 |
| 5,567,372 | 10/1996 | Nohr et al. | 264/103 |
| 5,683,707 | 11/1997 | Johnson | 424/407 |
| 5,686,088 | 11/1997 | Mitra et al. | 424/404 |
| 5,714,430 | 2/1998 | Gehrer et al. | 502/347 |

FOREIGN PATENT DOCUMENTS 62221445  9/1987  Japan .

*Primary Examiner*—Neil S. Levy
*Attorney, Agent, or Firm*—Chen Patents

[57] ABSTRACT

An inorganic anticmirobial composition has the the formula $AB_2O_4$ wherein A and B are low temperature far infrared irradiating metals, A is Mg, Zn, Mn, Ni, Co, or Fe(II), B is Al, Cr(III), Mn(III) or Fe(III), and O is oxygen. An antimicrobial article is made by coating said composition on a porous honeycomb-shaped substrate. An organic antimicrobal article is made from a quarternary ammonium salt coated on a porous honeycomb-shaped substrate. Processes of making the antimicrobial articles are provided.

13 Claims, 1 Drawing Sheet

♦ - Experiment of Honeycomb w/o coating of Quaternary Ammonium Salt (performed simultaneously with ▫ ,Experiment of Honeycomb treated with Quaternary Ammonium Salt for *Legionella pneumophila*).

▫ - Experiment of Honeycomb treated with Quaternary Ammonium Salt for *Legionella pneumophila*.

▲ - Experiment of Honeycomb treated with Quaternary Ammonium salt for *Salmonella typhimurium*.

⊙ - Experiment of Honeycomb treated with Quaternary Ammonium salt for *Escherichia coli*.

ANTIMICROBIAL COMPOSITION SUPPORTED ON A HONEYCOMB-SHAPED SUBSTRATE

BACKGROUND OF THE INVENTION

1. Field of the Invention

This invention relates to a novel antimicrobial inorganic composition and articles coated with the inorganic composition, and an organic antimicrobial composition, and a process of making such articles. More specifically, it relates to a composition comprising low temperature far infrared irradiating metals supported on a porous honeycomb shaped substrate, and an organic quaternary ammonium salt bonded on a porous honeycomb-shaped substrate.

2. Prior Art

Antimicrobial metals have been known to be incorporated into paints and fibers for industrial or home applications. Organic quaternary ammonium silane has been shown to have anti-algae properties. The following patents show the use of silver, copper, and zinc in antimicrobial substances, and the use of organosilicon compounds.

U.S. Pat. No. 3,865,728 discloses an organosilicon compound coated on a fibrous substrate and then heated to 65–100 degrees C. The resulting product is used for control of algae in aquarium tanks.

U.S. Pat. No. 5,147,686 discloses an antimicrobial powder made by coating a titanium oxide substrate with antimicrobial metals including copper, zinc or alloys of Cu—Zn, Cu—Ag, Cu—Al, Cu—Sn or the combination of these metals. The composition is useful against various microorganisms such as *E. Coli, Salmonella typhimurium*, and others. The coated substrate is fired at 400 degrees C. The powder form of this product is intended to be incorporated into a resin.

U.S. Pat. No. 5,151,122 relates to an antibacterial ceramic material. Various ceramics such as zeolite or alumina or clay are described as being fired at temperatures as high as 1200–1300 degrees C. so as to lock in the absorbed antibacterial metals such as silver, copper, or zinc. The patent further suggests that the product can be added to a resin which can be molded into any shape.

U.S. Pat. No. 5,415,775 relates to an ultrafiltration membrane consisting of alumina and titanium dioxide which has been sintered at 1000–1500 degrees C. and then coated with metal oxide. The membrane exhibits anti-bacterial properties.

U.S. Pat. Nos. 5,618,762, 5503,840, and 5,595,750 variously show Ag, Cu, Zn, Pt, Cd, Cr as antibacterial components including protective coatings.

None of the above patents shows an antimicrobial composition as disclosed herein. Furthermore, none of the above patents addresses the problem of keeping streams, water reservoirs, public baths, and fish farms clear of harmful micro-organisms including algae or bacteria. In addition to their antimicrobial properties, the articles of the present invention show high efficacy due to the honeycomb structure of the substrate which provides a multitude of antimicrobial sites per unit volume and prolonged antimicrobial efficacy in flowing air or water due to strong adhesion of the antimicrobial component on the substrate, without any adverse environmental effects such as are encountered when chemical pesticides, bactericides or herbicides are used.

The object of this invention is to provide antimicrobial articles having coated thereon a novel metal composition or an organic quaternary ammonium salt according to a specific process to eliminate harmful microbes such as *E. coli, Salmonella typhimurium*, and Saccharomycetes such as *Saccharomyces cerevisiae, Candida albicans*; Algae groups, such as Blue Green Algae, Brown Algae, and Green Algae, and Bacteria such as *Chaetomium globosum, Penicillium funiculosum* including *Legionella pneumophila*. Another object is to provide inexpensive articles having the shape of porous honeycombs treated with the antimicrobial substances of this invention. Such articles can be placed in nets or cages in streams, rivers or stationary bodies of water to eliminate harmful microbes. Still another object is to provide methods to prolong the life of such articles, thereby increasing and prolonging antimicrobial effectiveness. These objects of the invention will become apparent from the following description.

SUMMARY OF THE INVENTION

The articles of this invention are porous honeycomb-shaped substrates having coated theron inorganic or organic antimicrobial components. The inorganic component is selected from the Low Temperature Irradiating Far Infrared Material, herein referred to as metal composition. Said metal composition comprises metals capable of emitting far infrared radiation having a wavelength of from 3 to 30 microns below 60° C., which eliminates microbes. The metal composition has the general formula: $AB_2O_4$ of a regular spinel structure. It is to be noted that A and B are not chemical symbols. A is magnesium, divalent iron, nickel, manganese, cobalt or zinc. B is aluminum, trivalent iron, trivalent manganese, or trivalent chromium. O is oxygen. The composition may contain one or more of the following compounds: ferric oxide, ferric sulfide, zinc oxide, calcium oxide, titanium oxide, cupric oxide, aluminum oxide, aluminum sulfide, strontium oxide, and tantalum oxide as impurites.

The organic antimicrobial component is a quaternary ammonium salt having the formula:

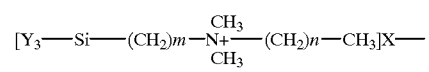

wherein m+n is 16 to 19, m is 1 to 6, and n is 13 to 17; or m+n is 20 to 23, m is 4 to 11 and n is 9 to 17; X is halogen; and Y is a hydrolyzable radical or hydroxy group.

The porous substrate of the antimicrobial article in accordance with this invention is sodium silicate, or diatomaceous earth or a ceramic material or siliceous clay or material comparable to silicon dioxide or aluminum oxide, which has been made into a honeycomb structure either by molding or extruding. The substrate is impregnated with either one of the above antimicrobial substances and calcined at a predetermined temperature.

DETAILED DESCRIPTION OF THE INVENTION

The Inorganic Antimicrobial Article

Figure 1:
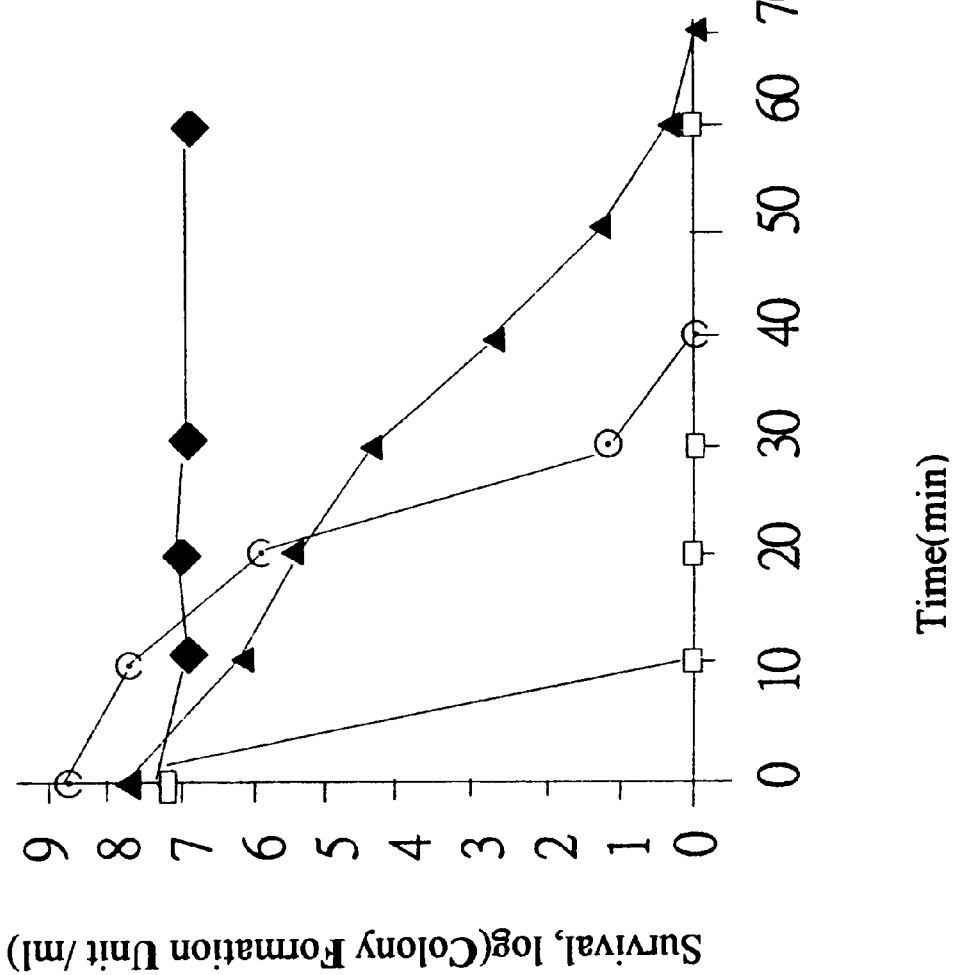
FIG. 1 shows the surival rate of the bacteria in accordance with the invention.

The substrate of the antimicrobial article is made of siliceous clay, ceramic or Boehmite powder mixed with water to form a slurry and extruded into a honeycomb-shaped preformed substrate having high porosity (herein referred to as preformed substrate). This preformed substrate has about 400 cells per square inch, providing a large surface area for the deposition of antimicrobial material. An alternative substrate may be made from a polymer material having the honeycomb shape and coated with the substrate material.

In fabricating the antimicrobal inorganic article using the metal composition as the antimicrobial component, the metal composition is blended with an appropriate bonding agent to form a soaking slurry or solution. A preformed substrate is impregnated with the soaking slurry The metal composition can be $MgFe_2O_4.Zn\ Fe_2O_4$., $FeCr_2O_4.MnFe_2O_4$ or any combination of metals selected from the A and B groups.

The bonding agent to be mixed with the metal composition can be an alkali metal silicate, such as sodium silicate. The metal composition should be 10–75%, preferably 25–50% by weight of the mixture.

Alternatively, the metal composition of this invention may be blended with the powder substrate directly, without soaking, and then molded into a honeycomb-shape, and calcined. The metal composition should be 10–85% of the total weight of the mixture, preferably 25–75%. The impregating process is preferred to the blending process.

The impregnated substrate is calcined at a temperature of 700–1100° C., preferably 800–1000° C. The calcining time is not critical; it can be based upon the size the articles.

The Organic Antimicrobial Article

Quarternary ammonium organosiloxane salt (herein referred to as quaternary ammonium salt) used as algicide by coating on a fibrous material as shown in U.S. Pat. Nos. 3,817,452 and 3,865,728 forms no part of this invention. Rather, this invention provides a new method of preparing an antimibrobial article. Moreover, the article kills not only algae but also bacteria. The relevant portions of the above patents are incorporated herewith by reference.

In the process of this invention, the quaternary ammonium salt is dissolved in water to form a moiety of —Si (OH)$_3$ and the preformed substrate is soaked in the solution. The moiety of the quarternay ammonium salt reacts with the $SiO_2$ of the substrate thereby forming a strong bond. 3-(Trimethoxysilyl)-propyldimethyloctadecyl ammonium chloride is representative of the group of silyl quaternary ammonium salts that may be used in the instant application.

It has been found that in the process of making the organic antimicrobial article of this invention, a special calcining aid can be used to enhance the adhesion or bonding of the quarternary ammonium salt to the preformed substrate. The calcining aid is aluminum oxide with high pore surface per unit volume, such as Boehmite, which is available from Condea Corporation in Germany. Other calcining aids can be $SiO_2$ or $SiO_2Al_2O_3$.

In the preparation of the organic antimicrobial article, aluminum oxide is mixed with water in the ratio of 1:1 to 1:10 by weight. An acid such as nitric, hydrochloric, or oxalic acid is added to adjust the pH to 3–6. After the mixture is ground to a gelatinous solution, the porous preformed substrate (as first described in conntection with the inorganic antimicrobial article ) is dipped into the gelatinous solution. This calcining-aid-coated preformed substrate is then calcined at 400 to 1500° C., preferably at 500 to 800° C.

Quaternary ammonium salt is dissolved in a solvent selected from the group consisting of water, alcohols, ketones, esters, hydrocarbons and chlorinated hydrocarbons in a concentration of about 0.05 to 20%, preferably 0.3 to 0.6% by weight. Water is the preferred solvent. The calcined substrate as prepared from above is impregnated with the quaternary ammonium salt solution until saturated or 50% of the solution is absorbed. The impregnated substrate is then dried at 50 to 200° C., preferably at 60 to 150° C. to form the organic antimicrobial article. Drying time depends on the size of the substrate.

The antimicrobial articles of this invention may be placed in water to kill microbes in, for example, cooling water. They may be placed in circulating air in air conditioning system to sterilize the air. After a period of use, the articles may be regenerated by flushing with clean water or vibrated with a ultrasonic device to remove any accumulated debris.

The following examples illustrate the preparation of the antimicrobial articles of this invention and their efficacy.

EXAMPLE 1

Preparation of the Inorganic Antimicrobial Articles 25 parts by weight of the metal composition $MgFe_2O_4$ and 75 parts by weight of 35 weight percent sodium silicate solution are mixed to form a uniform slurry, which is used to impregnate the preformed honeycomb-shaped substrate. Excess suspension is drained and the remainder dried by air blowing. The coated substrate is calcined at 800–900° C.

EXAMPLE 2

Process for Producing Inorganic Antimicrobial Articles

The metal composition $ZnCr_2O_4$ is mixed with powder substrate and sodium silicate in a 3:1 ratio by weight in the presence of an appropriate amount of water, forming a slurry, which is molded into honeycomb shape, and calcined at 900–1100° C. to produce the inorganic antimicrobial article.

EXAMPLE 3

Process Producing Organic Antimicrobial Article

Into 100 of 0.5 wt. % aqueous solution of 3-(trimethoxysilyl)-propyldimethyloctadecyl ammonium chloride, there is dipped a 50 g piece of the porous preformed substrate to soak until saturated. At least 50% of the solution should be absorbed. The piece of soaked substrate is dried at 100° C. for about 30 min. to allow chemical bonding to occur.

EXAMPLE 4

Test for Bonding Strength for Inorganic Antimirobial Article (metal composition coated on porous preformed substrate)

A uniform soaking slurry of the metal composition was made according to Example 1. The dry weight (A1) of each of the ten 10 pieces of the preformed substrate of about the same dimensions from the same batch was recorded The substrate pieces were soaked in the soaking slurry. All the soaked pieces were calcined under same conditions as described in the Example 1. The weight of each piece of the calcined substrates were recorded as (A2). The incremental weight, (A2–A1), represents the coating weight. The calcined substrate pieces were placed in an ultrasonic wash tank and subjected to vibration for one minute under 75 W power input and dried. Each substrate piece was weighed as weight(B). (B–A1) is the coating weight after vibration. The percent of adhesion of the coating equals (B–A1)/(A2–A1)× 100. The calculated result is shown in Table 1.

TABLE 1

| Sample | Percent adhesion |
|---|---|
| 1 | 97 |
| 2 | 98 |
| 3 | 99 |
| 4 | 99 |
| 5 | 99 |
| 6 | 98 |
| 7 | 99 |
| 8 | 100 |
| 9 | 99 |
| 10 | 98 |
| Average | 98.6 |

EXAMPLE 5

Test for Adhesion of Coating on Organic Antimicrobial Article. (quaternary ammonium salt on substrate)

Bromophenol blue changes color from violet to light blue to dark blue depending on the concentration of quarternary ammonium salt present in the water. A series of ten color standard solutions was prepared by dissolving the quarternary ammonium salt in the amount of 0, 0.1, 0.25, 0.5, 1.0, 2, 5, 5, 10, 15, and 20 wt. %×$10^{-4}$ in 500 cc of water. A fixed amount of bromophenol is added to each of the standard solutions to develop a series of color standards to which the sample is compared.

Ten samples of the organic antimicrobial articles were prepared as in Example 3 and the coated salt weight of each sample was recorded by weighing the coated, calcined article and the preformed substrate. The samples were placed in ten beakers. To each of the beakers, 500 cc of water were added. Each beaker was subjected to succesive ultrasonic vibration as in Example 4 for 0.5, 1, 2, 5, 10, 20, and 30 hours. After each interval of vibration, the vibration operation was stopped; the sample was taken out of each beaker and rinsed. To the remaining solution in each beaker, the same amount of bromophenol blue as used in the standard solution was added to develop different colors. This developed color is compared with the standard to determine the concentration of the quarternary ammonium salt dissolved. After each sample is initially vibrated for 0.5 hr, the sample was rinsed and immersed into its beaker filled with fresh water and subject to vibration for a subsequent periord, i.e. 1 hr. Again the dissovled quarternary ammonium salt was determined likewise. This procedure was repeated for each sample until the 30-hr vibration. The results are shown in the following table

TABLE 2

| | Ratio %** Time (hr.) | | | | | | |
|---|---|---|---|---|---|---|---|
| Number | 0.5 | 1 | 2 | 5 | 10 | 20 | 30 |
| 1 | 1.0 | 0.5 | 0.5 | 0.5 | 0.0 | 0.0 | 0.0 |
| 2 | 0.5 | 0.5 | 0.5 | 0.5 | 0.0 | 0.0 | 0.0 |
| 3 | 0.5 | 0.5 | 1.0 | 0.0 | 0.0 | 0.0 | 0.0 |
| 4 | 1.0 | 0.5 | 0.5 | 0.5 | 0.0 | 0.0 | 0.0 |
| 5 | 0.5 | 0.5 | 1.0 | 0.5 | 0.0 | 0.0 | 0.0 |
| 6 | 1.0 | 0.5 | 0.5 | 0.5 | 0.0 | 0.0 | 0.0 |
| 7 | 0.5 | 0.5 | 0.5 | 0.5 | 0.0 | 0.0 | 0.0 |
| 8 | 0.5 | 0.5 | 1.0 | 0.5 | 0.0 | 0.0 | 0.0 |
| 9 | 0.5 | 0.5 | 1.0 | 0.0 | 0.0 | 0.0 | 0.0 |
| 10 | 0.5 | 0.5 | 1.0 | 0.5 | 0.0 | 0.0 | 0.0 |
| Average | 0.65 | 0.5 | 0.75 | 0.35 | 0.0 | 0.0 | 0.0 |

Note: Marked thus ** means the % ratio of the dissolved Quaternary Ammonium Salt in water vs. The Quaternary Ammonium Salt originally bonded on each Honeycomb Substrate.

It is seen that the coated salt according to this invention initially loses under two percent on average and after 10 hour vibration, nothing is dissolved. and about 98% of the salt remains coated on the preformed substrate.

EXAMPLE 6

Efficacy of Inorganic Antimicrobial Article

Water samples from the pond of a fish farm were collected. The water was clear but some algae were growing at the bottom of the pond. The water was filtered with gauze. Four aquarium tanks 30 cm×20 cm×25 cm (length, width, height) numbered A, B, C and D were each filled with about 12 liters of the filtered water with the level of the water at 20 cm.

In tank A and C, the inorganic antimicrobial article having the metal composition coated thereon as described in Example 1 were placed, while tanks B and D received no inorganic antimicrobial article. The four tanks were left outdoors exposed to full sun. The tanks were covered with a sheet of transparent glass to prevent objects from falling in while allowing air to pass through.

Every other day a 30-cm ruler with 1 mm divisions was inserted into the water to observe and measure the variation and depth of visibility. Ths results are shown in Table 3.

TABLE 3

| | Time, days | | | | | | | | |
|---|---|---|---|---|---|---|---|---|---|
| | 1 | 3 | 5 | 7 | 9 | 11 | 13 | 15 | 17 |
| Tank | Visibility, in cm from surface of water | | | | | | | | |
| A | 20 | 20 | 20 | 20 | 20 | 20 | 20 | 20 | 20 |
| B | 20 | 20 | 16–18 | 12–15 | 8–9 | 4–5* | *** | *** | *** |
| C | 20 | 20 | 20 | 20 | 20 | 20 | 20 | 20 | 20 |
| D | 20 | 20 | 15–18 | 12–14 | 7–8* | 4** | *** | *** | *** |

*small amount of moss on tank wall.
**moss grew on tank wall, but not covered fully
***tank wall full of moss Tanks A and C were free of moss after 3 months.

EXAMPLE 7

Efficacy of Organic Antimicrobial Article

*Escherichia coli, Salmonella typhimurium* and *Legionella pneumophila* were incubated at 35° C. for 24 hours and the cell counts were determined. The antimicrobial articles as prepared in Example 3, and subjected to 10 hours of ultrasonic vibration. These treated articles and one preformed substrate were sterilized in an oven at 100° C. for 3 hours.

The three prepared porous articles were then hung in three sterile 500-ml beakers with magnetic stirring rods placed at the bottom. 500 ml of water-diluted cell suspension (around 2.0×$10^7$ CFU/ml) of each of the bacteria was poured into the beakers. The suspension was then stirred to create a swirl on top of the liquid. Cell counts of the suspensions were made at 0, 10, 20, 30, 40, 50, 60 and 70 minutes.

A control experiment was made with the sterile preformed substrate without coating of the quarternary ammonium salt. The substrate was suspended in a sterile beaker provided with magnetic stirring rod. A 500 ml of water with $2.0 \times 10^7$ CFU/ml of *Legionella pneumophila* was added to this beaker. All the beakers are incubated under same conditions The survival curve of *Escherichia coli, Salmonella typhimurium* and *Legionella pneumophila* suspended in water in the presence of the antimicrobial articles of this invention is shown in FIG. 1. The control is shown as diamond in FIG. 1.

CONCLUSION

The novelty of the antimicrobial articles of this invention has been illustrated firstly in a new metal composition of which the irradiating property exhibits antimicrobial power which does not rely on physical contact in order to kill microbes; secondly in a new process of adhesion of antimicrobial components on a porous honeycomb-shaped substrate, and thirdly, the antimicrobial effectiveness of the articles of this invention is against many species of microbes.

The foregoing is considered illustrative of the principles of this invention. Numerous modifications and changes may occur to those skilled in the art. It is not desired to limit the invention to the specific examples as described. Accordingly, all suitable modifications fall within the scope of the appended claims.

What is claimed is:

1. An antimicrobial composition comprising: a calcined, porous, honeycomb-shaped mixture of 10–85% by weight of a metal composition having a formula $AB_2O_4$ wherein A is selected from the group consisting of magnesium, divalent iron, manganese, nickel, cobalt and zinc; B is selected from the group consisting of aluminum, trivalent iron, trivalent manganese and trivalent chromium; and O is oxygen, and 15–90% of a substrate selected from the group consisting of siliceous clay, ceramic, silicon oxide, aluminum oxide, sodium silicate, and any combination thereof.

2. The composition of claim 1, wherein A and B are low temperature far infrared irradiating metals, and the formula has a spinel structure.

3. A porous calcined antimicrobial article comprising a honeycomb-shaped substrate and coated thereon an antimicrobial metal composition having a formula $AB_2O_4$, wherein A is selected from the group consisting of magnesium, divalent iron, manganese, nickel, cobalt and zinc; B is selected from the group consisting of aluminum, trivalent iron, trivalent manganese and trivalent chromium; and O is oxygen.

4. The article of claim 3 further comprising alkali silicate, as a bonding agent.

5. The article of claim 4, wherein the alkali silicate is sodium silicate.

6. The antimicrobial article of claim 3 wherein the honeycomb-shaped substrate is made from a material selected from the group consisting of silicon oxide, ceramic, siliceous clay and the combination thereof.

7. A method of eliminating harmful microbes in a fluid comprising placing in said fluid a porous antimicrobial article of a calcined, honeycomb-shaped substrate impregnated with a solution of an organosilyl quaternary ammonium salt having the formula $$[Y_3—Si—(CH_2)_m—\overset{CH_3}{\underset{CH_3}{N^+}}—(CH_2)_n—CH_3]X—$$

wherein m+n is 16 to 19, m is 1 to 6, and n is 13 to 17; or m+n is 20 to 23, m is 4 to 11 and n is 9 to 17; X is halogen; and Y is a hydrolyzable radical or hydroxy group.

8. The method of claim 7 wherein the honeycomb-shaped substrate is made from a material selected from a group consisting of silicon oxide, ceramic, siliceous clay, and the combination thereof.

9. The method of claim 7 wherein the honeycomb-shaped substrate is a polymer honeycomb coated with a material selected from the group consisting of silicon oxide, ceramic, siliceous clay, and the combination thereof.

10. The method of claim 7 wherein the quaternary ammonium salt is 3-(trimethoxysilyl)-propyldimethyloctadecyl ammonium chloride.

11. The method of claim 7, further comprising a calcining aid selected from the group consisting of aluminum oxide, silicon dioxide and the combination thereof.

12. The method of claim 11, wherein the calcining aid is coated on the honeycomb-shaped substrate.

13. The method of claim 7 wherein the article comprises at least 1 part by wt. of 3-(trimethoxysilyl)-propyldimethyloctadecyl ammonium chloride solution coated on 200 parts by wt. of the calcined. porous. honeycomb-shaped substrate selected from the group consisting of siliceous clay; silicon oxide, aluminum oxide, sodium silicate, and any combination thereof.

* * * * *

UNITED STATES PATENT AND TRADEMARK OFFICE
CERTIFICATE OF CORRECTION

PATENT NO. : 6,051,246

DATED : April 18, 2000

INVENTOR(S) : Shiau et al

It is certified that error appears in the above-identified patent and that said Letters Patent is hereby corrected as shown below:

On the title page of the above mentioned patent, second column, under 'Attorney, Agent, or Firm', the firm name should be CHENPATENTS.

In column 7, line 15, after Fig. 1, the missing paragraph is as follows: Fig. 1 shows the survival rate of each bacteria. *Legionelia pneumophila* dies within 10 minutes in contact with the antimicrobial article. *E.coli* dies after 40 minutes and *Salmonella typimurium* after about 60 minutes. The control shows the same rate of survival of *Legionelia pneumophila*.

Signed and Sealed this

Twenty-ninth Day of May, 2001

*Attest:*

NICHOLAS P. GODICI

*Attesting Officer*   Acting Director of the United States Patent and Trademark Office